(12) United States Patent
Harper et al.

(10) Patent No.: US 11,154,345 B2
(45) Date of Patent: Oct. 26, 2021

(54) SYSTEM AND METHOD FOR TISSUE SEALING

(71) Applicant: COVIDIEN LP, Mansfield, MA (US)

(72) Inventors: Jennifer S. Harper, Westminster, CO (US); Meghan Marie Collins Long, Centennial, CO (US)

(73) Assignee: Covidien LP, Mansfield, MA (US)

( * ) Notice: Subject to any disclaimer, the term of this patent is extended or adjusted under 35 U.S.C. 154(b) by 707 days.

(21) Appl. No.: 16/055,239

(22) Filed: Aug. 6, 2018

(65) Prior Publication Data

US 2018/0338788 A1 Nov. 29, 2018

Related U.S. Application Data

(62) Division of application No. 12/639,210, filed on Dec. 16, 2009, now Pat. No. 10,039,588.

(51) Int. Cl.
*A61B 18/14* (2006.01)
*A61B 18/12* (2006.01)
*A61B 18/00* (2006.01)

(52) U.S. Cl.
CPC ...... *A61B 18/1206* (2013.01); *A61B 18/1442* (2013.01); *A61B 2018/0063* (2013.01);
(Continued)

(58) Field of Classification Search
CPC ............ A61B 18/1206; A61B 18/1442; A61B 2018/0063; A61B 2018/00678;
(Continued)

(56) References Cited

U.S. PATENT DOCUMENTS 6,306,131 B1 10/2001 Hareyama et al.
6,436,096 B1 8/2002 Hareyama
(Continued)

FOREIGN PATENT DOCUMENTS

DE 179607 C 3/1905
DE 390937 C 3/1924
(Continued)

OTHER PUBLICATIONS

International Search Report EP08006733.3 dated Jul. 28, 2008.
(Continued)

*Primary Examiner* — Michael F Peffley
*Assistant Examiner* — Samantha M Good
(74) *Attorney, Agent, or Firm* — Carter, DeLuca & Farrell LLP

(57) ABSTRACT

An electrosurgical system includes an energy source adapted to supply energy to tissue. The energy source includes a microprocessor configured to execute a tissue treatment algorithm configured to control the supply of electrosurgical energy to tissue and process a configuration file including at least one parameter of the tissue treatment algorithm. The at least one parameter is adjustable to effect a tissue seal result. The microprocessor generates a target impedance trajectory based on at least one parameter of the tissue treatment algorithm and is further configured to drive tissue impedance along the target impedance trajectory by adjusting the supply of energy to tissue to substantially match tissue impedance to a corresponding target impedance value. The system also includes an electrosurgical instrument including at least one active electrode adapted to apply electrosurgical energy to tissue.

15 Claims, 4 Drawing Sheets

(52) U.S. Cl.
CPC .............. *A61B 2018/00678* (2013.01); *A61B 2018/00684* (2013.01); *A61B 2018/00702* (2013.01); *A61B 2018/00875* (2013.01)

(58) Field of Classification Search
CPC ........... A61B 2018/00684; A61B 2018/00702; A61B 2018/00875
See application file for complete search history.

(56) References Cited

U.S. PATENT DOCUMENTS

| | | |
|---|---|---|
| 6,511,476 B2 | 1/2003 | Hareyama |
| 6,648,883 B2 | 11/2003 | Francischelli et al. |
| 6,989,010 B2 | 1/2006 | Francischelli et al. |
| 7,137,980 B2 | 11/2006 | Buysse et al. |
| 7,250,048 B2 | 7/2007 | Francischelli et al. |
| 7,367,972 B2 | 5/2008 | Francischelli et al. |
| D574,323 S | 8/2008 | Waaler |
| 7,956,620 B2 | 6/2011 | Gilbert |
| 7,972,328 B2 | 7/2011 | Wham et al. |
| 8,105,323 B2 | 1/2012 | Buysse et al. |
| 8,152,802 B2 | 4/2012 | Podhajsky et al. |
| 8,162,932 B2 | 4/2012 | Podhajsky et al. |
| 8,167,875 B2 | 5/2012 | Podhajsky et al. |
| 8,174,267 B2 | 5/2012 | Brannan et al. |
| 8,180,433 B2 | 5/2012 | Brannan et al. |
| 8,211,100 B2 | 7/2012 | Podhajsky et al. |
| 8,216,223 B2 | 7/2012 | Wham et al. |
| 8,226,639 B2 | 7/2012 | Podhajsky et al. |
| 8,231,553 B2 | 7/2012 | Joseph et al. |
| 8,235,917 B2 | 8/2012 | Joseph et al. |
| 8,242,782 B2 | 8/2012 | Brannan et al. |
| 8,248,075 B2 | 8/2012 | Brannan et al. |
| 2005/0004564 A1 | 1/2005 | Wham et al. |
| 2005/0101948 A1 | 5/2005 | Harano et al. |
| 2005/0101951 A1 | 5/2005 | Wham et al. |
| 2005/0203504 A1 | 9/2005 | Wham et al. |
| 2007/0038209 A1 | 2/2007 | Buysse et al. |
| 2007/0173803 A1 | 7/2007 | Wham et al. |
| 2007/0173804 A1 | 7/2007 | Wham et al. |
| 2007/0173805 A1 | 7/2007 | Weinberg et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0254077 A1 | 10/2009 | Craig |
| 2009/0292283 A1 | 11/2009 | Odom |
| 2010/0030210 A1 | 2/2010 | Paulus |
| 2010/0042093 A9 | 2/2010 | Wham et al. |
| 2010/0057076 A1 | 3/2010 | Behnke et al. |
| 2010/0063494 A1 | 3/2010 | Orszulak |
| 2010/0063497 A1 | 3/2010 | Orszulak |
| 2010/0082022 A1 | 4/2010 | Haley et al. |
| 2010/0082083 A1 | 4/2010 | Brannan et al. |
| 2010/0082084 A1 | 4/2010 | Brannan et al. |
| 2010/0094271 A1 | 4/2010 | Ward et al. |
| 2010/0094288 A1 | 4/2010 | Kerr |
| 2010/0179533 A1 | 7/2010 | Podhajsky |
| 2010/0179538 A1 | 7/2010 | Podhajsky |
| 2011/0028963 A1 | 2/2011 | Gilbert |
| 2011/0054460 A1 | 3/2011 | Gilbert |
| 2011/0060329 A1 | 3/2011 | Gilbert et al. |
| 2011/0071516 A1 | 3/2011 | Gregg |
| 2011/0071521 A1 | 3/2011 | Gilbert |
| 2011/0077631 A1 | 3/2011 | Keller |
| 2011/0112530 A1 | 5/2011 | Keller |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| EP | 0246350 A1 | 11/1987 |
| EP | 0267403 A2 | 5/1988 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0556705 A1 | 8/1993 |
| EP | 0608609 A2 | 8/1994 |
| EP | 0836868 A2 | 4/1998 |
| EP | 0870473 A2 | 10/1998 |
| EP | 0880220 A2 | 11/1998 |
| EP | 0882955 A1 | 12/1998 |
| EP | 1051948 A2 | 11/2000 |
| EP | 1366724 A1 | 12/2003 |
| EP | 1472984 A1 | 11/2004 |
| EP | 1810630 A1 | 7/2007 |
| EP | 1810633 A2 | 7/2007 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 2005040616 A | 2/2005 |
| JP | 2007195973 A | 8/2007 |
| JP | 2007195985 A | 8/2007 |
| SU | 166452 | 1/1965 |
| SU | 727201 A2 | 4/1980 |
| WO | 0211634 A1 | 2/2002 |
| WO | 0245589 A2 | 6/2002 |
| WO | 03090635 A1 | 11/2003 |
| WO | 2006050888 A1 | 5/2006 |

OTHER PUBLICATIONS

International Search Report EP08012503 dated Sep. 19, 2008.
International Search Report EP08013605 dated Feb. 25, 2009.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09009860 dated Dec. 8, 2009.
International Search Report EP09164754.5 dated Aug. 21, 2009.
International Search Report EP09169377.0 dated Dec. 15, 2009.
International Search Report EP09172749.5 dated Dec. 4, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
European Search Report for European Application No. 10195393 dated Mar. 11, 2011.

(56) References Cited

OTHER PUBLICATIONS

U.S. Appl. No. 10/406,690, filed Apr. 3, 2003, Klicek.
U.S. Appl. No. 10/573,713, filed Mar. 28, 2006, Wham.
U.S. Appl. No. 11/242,458, filed Oct. 3, 2005, Becker.
U.S. Appl. No. 12/184,556, filed Aug. 1, 2008, Paulus.
Office Action issued by the Canadian Patent Office corresponding to Canadian Patent Application No. 2,725,893; dated Jun. 23, 2016.
English Abstract of Japanese Laid-Open Publication No. 2007-195985.
Engliksh Abstract of Japanese Laid-Open Publication No. 2007-195973.
English Abstract of Japanese Laid-Open Publication No. 2005-040616.
Notice of Allowance for Japanese Application No. 2010-280159 dated May 13, 2015.
JPO Communication Summary Form dated May 13, 2015.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden, "Goertzel Alternative to the Fourier Transform": Jun. 1993 pp. 485-487 Electronics World; Reed Business Publishing, Sutton, Surrey, BG, vol. 99, No. 9, 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994), pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B. V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3, dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.

SYSTEM AND METHOD FOR TISSUE SEALING

CROSS-REFERENCE TO RELATED APPLICATION

This application is a divisional of U.S. patent application Ser. No. 12/639,210 filed on Dec. 16, 2009, now U.S. Pat. No. 10,039,588, the entire contents of which are incorporated by reference herein.

BACKGROUND

1. Technical Field

The present disclosure relates to an electrosurgical system and method for performing electrosurgical procedures. More particularly, the present disclosure relates to sealing tissue, wherein energy is administered to match measured impedance to a desired impedance.

2. Background of Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

Bipolar electrosurgery generally involves the use of forceps. A forceps is a pliers-like instruments that relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive plates that apply electrosurgical energy to the clamped tissue. By controlling the intensity, frequency, and duration of the electrosurgical energy applied through the conductive plates to tissue, the surgeon can coagulate, cauterize, and/or seal tissue.

Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, it has been determined that two predominant mechanical parameters must be accurately controlled: the pressure applied to the tissue; and the gap distance between the electrodes (i.e., the distance between opposing jaw members or opposing sealing plates). In addition, electrosurgical energy must be applied to the tissue under controlled conditions to ensure creation of an effective vessel seal.

SUMMARY

According to embodiments of the present disclosure, an electrosurgical system includes an energy source adapted to supply energy to tissue. The energy source includes a microprocessor configured to execute a tissue treatment algorithm configured to control the supply of electrosurgical energy to tissue and process a configuration file including at least one parameter of the tissue treatment algorithm. The at least one parameter is adjustable to effect a tissue seal result. The microprocessor generates a target impedance trajectory based on at least one parameter of the tissue treatment algorithm and is further configured to drive tissue impedance along the target impedance trajectory by adjusting the supply of energy to tissue to substantially match tissue impedance to a corresponding target impedance value. The system also includes an electrosurgical instrument including at least one active electrode adapted to apply electrosurgical energy to tissue.

According to another embodiment of the present disclosure, a method of performing an electrosurgical procedure includes the steps of adjusting at least one parameter of a tissue treatment algorithm configured to control the supply of energy to tissue to effect a desired burst pressure and supplying energy from an energy source to an electrosurgical instrument for application to tissue. The method also includes the steps of generating a target impedance trajectory based on measured impedance and at least one parameter of the tissue treatment algorithm and adjusting the supply of energy from the energy source to tissue to match tissue impedance to a target impedance value. The method also includes the step of adjusting the target impedance value to vary the desired burst pressure.

According to another embodiment of the present disclosure, a method of performing an electrosurgical procedure includes the steps of adjusting at least one parameter of a tissue treatment algorithm configured to control the supply of energy to tissue to effect a desired burst pressure and supplying energy from an energy source to an electrosurgical instrument for application to tissue. The method also includes the steps of generating a target impedance trajectory based on measured impedance and a predetermined rate of change of impedance and adjusting the supply of energy from the energy source to tissue to match tissue impedance to a target impedance value.

BRIEF DESCRIPTION OF THE DRAWINGS

Various embodiments of the present disclosure are described herein with reference to the drawings wherein.

DETAILED DESCRIPTION

Particular embodiments of the present disclosure will be described hereinbelow with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument or an open instrument.

It is envisioned the method may be extended to other tissue effects and energy-based modalities including, but not limited to ultrasonic, laser, microwave, and cryo tissue treatments. It is also envisioned that the disclosed methods are based on impedance measurement and monitoring but other tissue and energy properties may be used to determine state of the tissue, such as temperature, current, voltage, power, energy, phase of voltage and current. It is further envisioned that the method may be carried out using a feedback system incorporated into an electrosurgical system or may be a stand-alone modular embodiment (e.g., removable modular circuit configured to be electrically coupled to various components, such as a generator, of the electrosurgical system).

The present disclosure relates to a method for controlling energy delivery to tissue based on tissue feedback. If electrosurgical energy is being used to treat the tissue, the tissue characteristic being measured and used as feedback is typically impedance and the interrogatory signal is electrical in nature. If other energy is being used to treat tissue then interrogatory signals and the tissue properties being sensed vary accordingly. For instance the interrogation signal may be achieved thermally, audibly, optically, ultrasonically, etc. and the initial tissue characteristic may then correspondingly be temperature, density, opaqueness, etc. The method according to the present disclosure is discussed using electrosurgical energy and corresponding tissue properties (e.g., impedance). Those skilled in the art will appreciate that the method may be adopted using other energy applications.

The generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry adapted to generate radio frequency power specifically suited for various electrosurgical modes (e.g., cutting, blending, division, etc.) and procedures (e.g., monopolar, bipolar, vessel sealing).

Figure 1A:
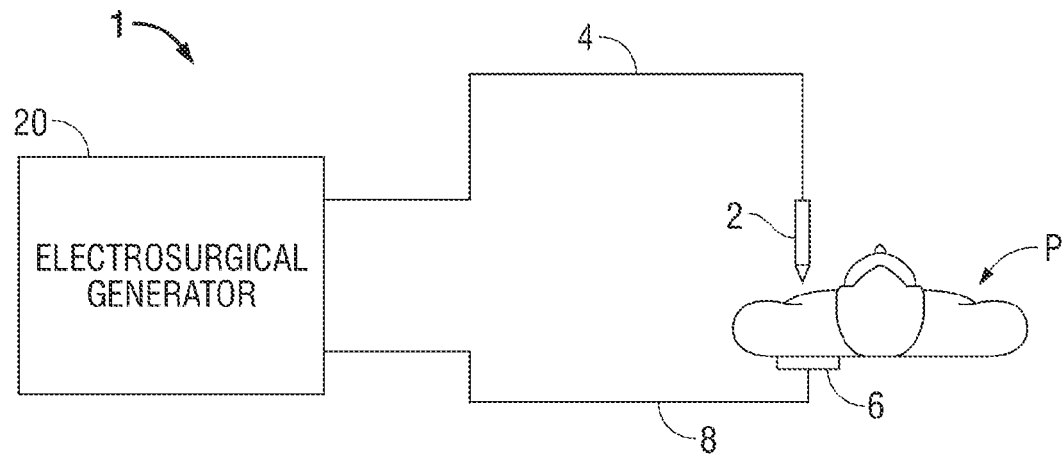
FIG. 1A is a schematic block diagram of a monopolar electrosurgical system in accordance with an embodiment of the present disclosure.

FIG. 1A is a schematic illustration of a monopolar electrosurgical system according to one embodiment of the present disclosure. The system includes an electrosurgical instrument 2 (e.g., monopolar) having one or more electrodes for treating tissue of a patient P (e.g., electrosurgical cutting, ablation, etc.). More particularly, electrosurgical RF energy is supplied to the instrument 2 by a generator 20 via a supply line 4, that is connected to an active terminal 30 (see FIG. 2) of the generator 20, allowing the instrument 2 to coagulate, seal, ablate and/or otherwise treat tissue. The energy is returned to the generator 20 through a return electrode 6 via a return line 8 at a return terminal 32 of the generator 20 (see FIG. 2). The active terminal 30 and the return terminal 32 are connectors configured to interface with plugs (not explicitly shown) of the instrument 2 and the return electrode 6, that are disposed at the ends of the supply line 4 and the return line 8, respectively.

Figure 1B:
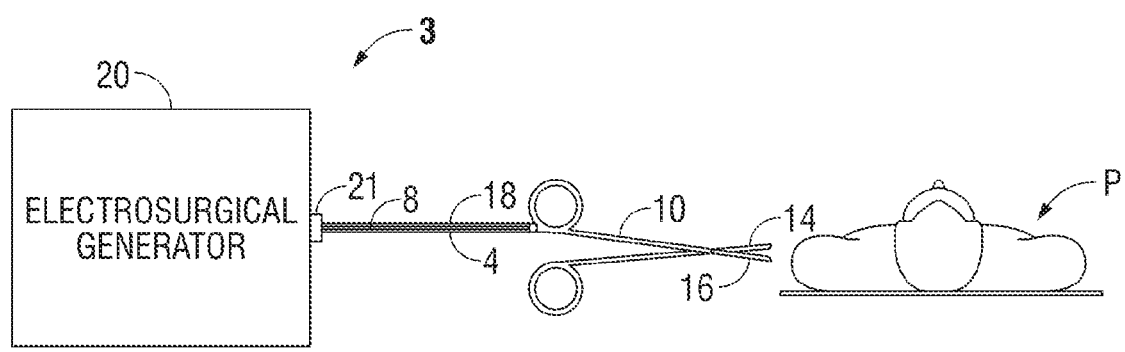
FIG. 1B is a schematic block diagram of a bipolar electrosurgical system in accordance with an embodiment of the present disclosure.

FIG. 1B is a schematic illustration of a bipolar electrosurgical system according to the present disclosure. The system includes a bipolar electrosurgical forceps 10 having one or more electrodes for treating tissue of a patient P. The electrosurgical forceps 10 includes opposing jaw members 14 and 16 having an active electrode and a return electrode (not explicitly shown), respectively, disposed thereon. The active and return electrodes are connected to the generator 20 through cable 18, which includes the supply and return lines 4, 8 coupled to the active terminal 30 and return terminal 32, respectively (see FIG. 2). The electrosurgical forceps 10 is coupled to the generator 20 at a connector 21 having connections to the active terminal 30 and return terminal 32 (e.g., pins) via a plug disposed at the end of the cable 18, wherein the plug includes contacts from the supply and return lines 4, 8.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform parameters (e.g., crest factor, duty cycle, etc.), and other parameters to achieve the desired waveform suitable for a particular task (e.g., coagulating, tissue sealing, intensity setting, etc.).

Figure 2:
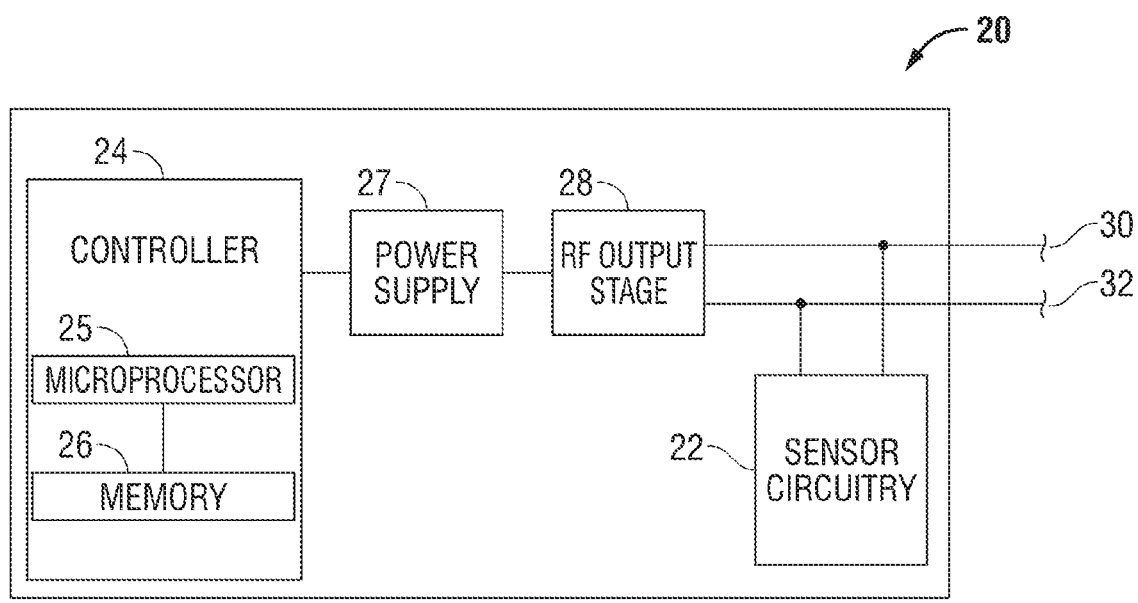
FIG. 2 is a schematic block diagram of a generator algorithm according to the present disclosure.

FIG. 2 shows a schematic block diagram of the generator 20 having a controller 24, a DC power supply 27, and an RF output stage 28. The power supply 27 is connected to a conventional AC source (e.g., electrical wall outlet) and is adapted to provide high voltage DC power to an RF output stage 28 that converts high voltage DC power into RF energy. RF output stage 28 delivers the RF energy to an active terminal 30. The energy is returned thereto via the return terminal 32.

The generator 20 may include a plurality of connectors to accommodate various types of electrosurgical instruments (e.g., instrument 2, electrosurgical forceps 10, etc.). Further, the generator 20 may be configured to operate in a variety of modes such as ablation, monopolar and bipolar cutting coagulation, etc. The generator 20 may also include a switching mechanism (e.g., relays) to switch the supply of RF energy between the connectors, such that, for example, when the instrument 2 is connected to the generator 20, only the monopolar plug receives RF energy.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the power supply 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme or feedback control loop is provided that includes a sensor circuitry 22 having one or more sensors for measuring a variety of tissue and energy properties (e.g., tissue impedance, tissue temperature, output current and/or voltage, etc.). The sensor circuitry 22 provides feedback to the controller 24. Such sensors are within the purview of those skilled in the art. The controller 24 then signals the power supply 27 and/or RF output stage 28, which then adjusts DC and/or RF power supply, respectively. The controller 24 also receives input signals from the input controls of the generator 20 or the instrument 10. The controller 24 utilizes the input signals to adjust power outputted by the generator 20 and/or performs other control functions thereon. In embodiments, sensor circuitry 22 (or an additional sensor circuitry (not shown)) may be disposed between RF output stage 28 and active terminal 30 to measure output current.

In particular, sensor circuitry 22 is adapted to measure tissue impedance. This is accomplished by measuring voltage and current signals and calculating corresponding impedance values as a function thereof at the sensor circuitry 22 and/or at the microprocessor 25. Power and other energy properties may also be calculated based on collected voltage and current signals. The sensed impedance measurements are used as feedback by the generator 20.

The method of sealing tissue according to the present disclosure is discussed below with reference to FIGS. 3 and 4. The method may be embodied in a software-based tissue treatment algorithm that is stored in memory 26 and is executed by microprocessor 25. The graph of FIG. 4 shows tissue impedance as a function of time to illustrate various phases that tissue undergoes during particular application of energy thereto. The decrease in tissue impedance as energy is applied occurs when tissue is being fused (e.g., vessel sealing), ablated, or desiccated. It is generally known that at the onset of electrical energy (i.e., during tissue fusion, ablation, or desiccation), tissue heating results in a decreasing impedance toward a minimum impedance value that is below an initial sensed impedance. Tissue impedance begins to rise almost immediately when tissue is being coagulated.

Prior to or during a tissue sealing procedure, a user may select or adjust particular variables or parameters of the tissue treatment algorithm to effect a desired quality for a vessel seal. The quality of a vessel seal may be determined quantitatively by burst pressure (e.g., the pressure necessary to burst tissue at the seal site). Burst pressure for a resulting tissue seal varies in accordance with particular parameters of the tissue treatment algorithm. The parameters of the algorithm may correspond to one or more phases of the algorithm and may include, for example without limitation, a current ramp rate parameter, an impedance ramp rate parameter, a shutoff or end tissue impedance parameter, a seal time or procedure time parameter, a burst pressure parameter, a maximum current, a tissue impedance detection, etc. These algorithm parameters may be selected/adjusted by the user through use of the input controls of the generator 20 and input into a configuration file that includes a variety of variables that control the algorithm, e.g., the parameters listed above. Certain variables of the configuration file may be adjusted based on the instrument being used and the settings selected by the user. One or more configuration files may be loaded from a data store included within controller 24.

Algorithm parameters, such as the algorithm parameters described above, may be adjusted and/or selected by a user to effect a desired burst pressure corresponding to a particular tissue seal quality. More specifically, by manipulating particular algorithm parameters relative to other algorithm parameters, the resulting quality of the tissue seal may be customized by the user. However, the adjustment of certain algorithm parameters to achieve a desired burst pressure, may result in added seal time to achieve the improved result. For example, the greater the burst pressure of a resulting tissue seal, the more seal time needed to achieve such burst pressure. The tissue treatment algorithm is configured to automatically make adjustments to appropriate algorithm parameters in response to and in proportion to algorithm parameters as they are adjusted by the user. In this manner, the user may simply select a preset burst pressure or seal time as a tissue sealing parameter and, in response, the tissue treatment algorithm adjusts other appropriate algorithm parameters proportionally to achieve the preset burst pressure. For example, as the user increases the desired burst pressure, the algorithm may automatically slow down a current ramp rate or an impedance ramp rate proportionally to achieve the desired burst pressure of the resulting tissue seal. Additionally or alternatively, the user may adjust a particular tissue sealing parameter (e.g., shutoff impedance, current ramp rate, impedance ramp rate, maximum current, impedance detection, etc.) and, in response, the tissue treatment algorithm adjusts related algorithm parameters proportionally to effect a desired seal time, seal quality, and/or burst pressure. Further, the tissue treatment algorithm may, in certain embodiments, generate a display, signal, or indication of the anticipated seal time, seal quality, and/or burst pressure that will result from the user selected parameter. For example, an indication may be provided via the display screen of the generator 20 as output information. Based on the output information (e.g., seal time), the user is given opportunity to make an informed revision or adjustment to algorithm parameters to increase or decrease seal time and/or burst pressure.

During phase I or the so-called "cook phase", which is a pre-heating or early desiccation stage, the level of current supplied to the tissue is sufficiently low and impedance of the tissue starts at an initial impedance value. As the level of current applied to tissue is increased or ramped upward at a predetermined rate, temperature therein rises and tissue impedance decreases. At a later point in time, tissue impedance reaches a minimum impedance value 210 that corresponds to tissue temperature of approximately 100° C., a boiling temperature of intra- and extra-cellular fluid. The rate at which current is ramped during phase I, for example, is an algorithm parameter that may be adjusted by the user and loaded into the configuration file. As the current ramp rate is adjusted to be slower or more gradual, the total seal time (e.g., time required to achieve a tissue seal) increases. However, as the current ramp rate is slowed or made more gradual, the resulting burst pressure also increases to improve seal quality. Once initiated, the ramping of current continues until one of two events occurs: 1) the maximum allowable current value is reached, or 2) the tissue "reacts". The term "tissue reaction" references a point at which intracellular and/or extra-cellular fluid begins to boil and/or vaporize, resulting in an increase in tissue impedance. In the case when the maximum allowable current value is reached, the maximum current value is maintained until the tissue "reacts". In the event that tissue reacts prior to reaching the maximum current value, the level of energy required to initiate a tissue "reaction" is processed and stored (e.g., in memory 26) and the tissue treatment algorithm moves to an impedance control state.

Phase II is a vaporization phase or a late desiccation phase, during which tissue has achieved a phase transition from having moist and conductive properties to having dry and non-conductive properties. In particular, as the majority of the intra- and extra-cellular fluids begin to rapidly boil during the end of phase I, tissue impedance begins to rise above the minimum impedance value 210. As sufficient energy is continually applied to the tissue during phase II, temperature rises beyond the boiling point coinciding with minimum impedance value 210. As temperature continues to rise, tissue undergoes a phase change from a moist state to a solid state and eventually to a dried-out state. As additional energy is applied, tissue is completely desiccated and eventually vaporized, producing steam, tissue vapors, and charring. Those skilled in the art will appreciate that the impedance changes illustrated in FIG. 4 are illustrative of an exemplary electrosurgical procedure and that the present disclosure may be utilized with respect to electrosurgical procedures having different impedance curves and/or trajectories.

Once it is established that tissue has reacted, the algorithm calculates a predefined target impedance trajectory (e.g., downward in phase I, upward in phase II, etc.) based on the actual impedance and a predetermined rate of change of the impedance (dZ/dt). The tissue treatment algorithm controls output of the generator 20 as a function of tissue impedance by driving tissue impedance along the target impedance trajectory by adjusting the power output level to substantially match tissue impedance to a corresponding target impedance value. While the tissue treatment algorithm continues to direct the RF energy to drive the tissue impedance to match the specified trajectory, the algorithm monitors the tissue impedance to make the appropriate corrections.

As previously described, the configuration file includes a variety of predefined values that control the tissue treatment algorithm. In particular, an ending impedance value 220 and a reaction timer may be loaded into the configuration file. The ending impedance value 220, for example, is an algorithm parameter that may be adjusted by the user and loaded into the configuration file. As the ending impedance value 220 is increased, the total seal time (e.g., time required to achieve a tissue seal) increases and the resulting burst pressure also increases, thereby improving the quality of the tissue seal. The desired rate of change of the impedance (dZ/dt) is also an algorithm parameter that may be adjusted by the user and loaded into the configuration file. As the desired rate of change of the impedance during phase II is slowed, the total seal time (e.g., time required to achieve a tissue seal) increases and the resulting burst pressure also increases, thereby improving the quality of the tissue seal.

The ending impedance value 220 in conjunction with an offset impedance value are used to calculate a threshold impedance value that denotes completion of treatment. In particular, application of electrosurgical energy to tissue continues until tissue impedance is at or above the threshold impedance. The threshold impedance is determined by adding the ending impedance value 220 and the offset impedance value. The ending impedance value 220 may range from about 10 ohms to about 1000 ohms above the lowest measured impedance reached.

The termination condition may also include applying electrosurgical energy for a predetermined period of time, e.g., reaction time, that is embodied by a predetermined reaction timer value loaded into the configuration file. This ensures that the treatment process does not over cook tissue. The ending impedance value 220 and the reaction timer may be hard-coded and may be selected automatically based on tissue type, the instrument being used, and/or the settings selected by the user. The ending impedance value 220 may be loaded at anytime during tissue treatment. Further, the ending impedance value 220 and the reaction timer may also be selected/adjusted by the user.

The algorithm determines whether tissue fusion is complete by monitoring the actual measured impedance rising above a predetermined threshold and staying above the predetermined threshold for a predetermined period of time. The threshold is defined as a specified level above the initial sensed impedance value and denotes completion of treatment. This determination minimizes the likelihood of terminating electrosurgical energy early when the tissue is not properly or completely sealed.

Figure 3:
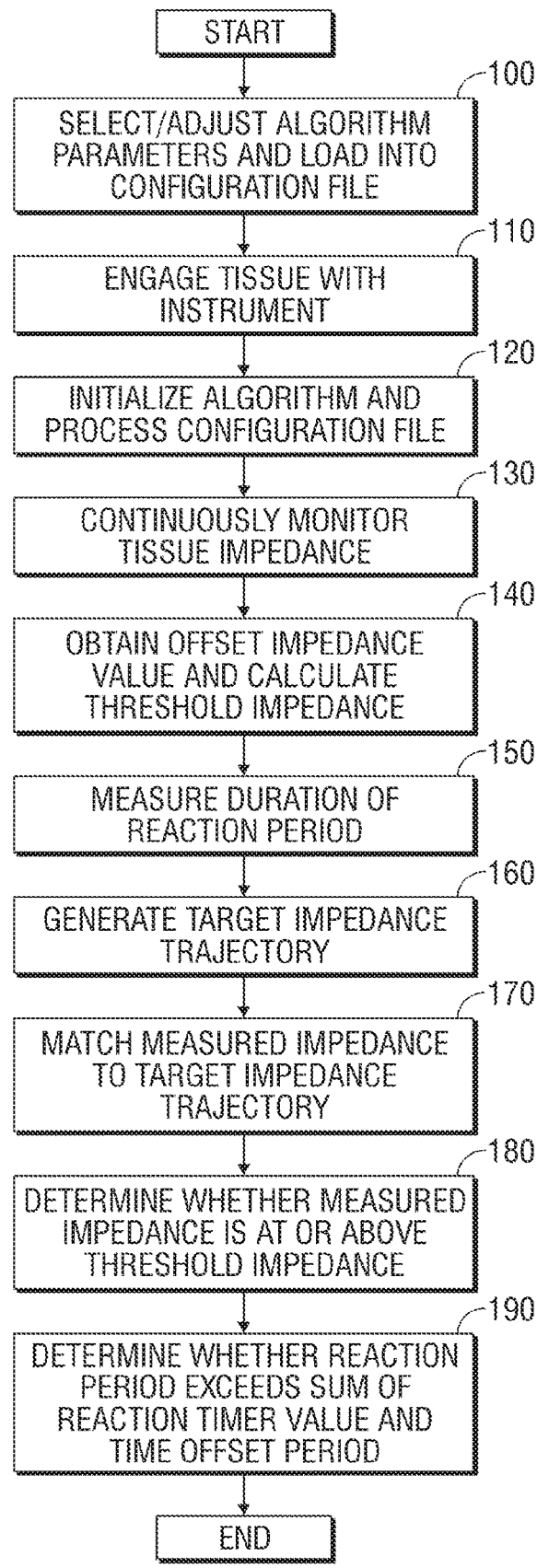
FIG. 3 shows a flow chart illustrating a method of performing an electrosurgical procedure.
Figure 4:
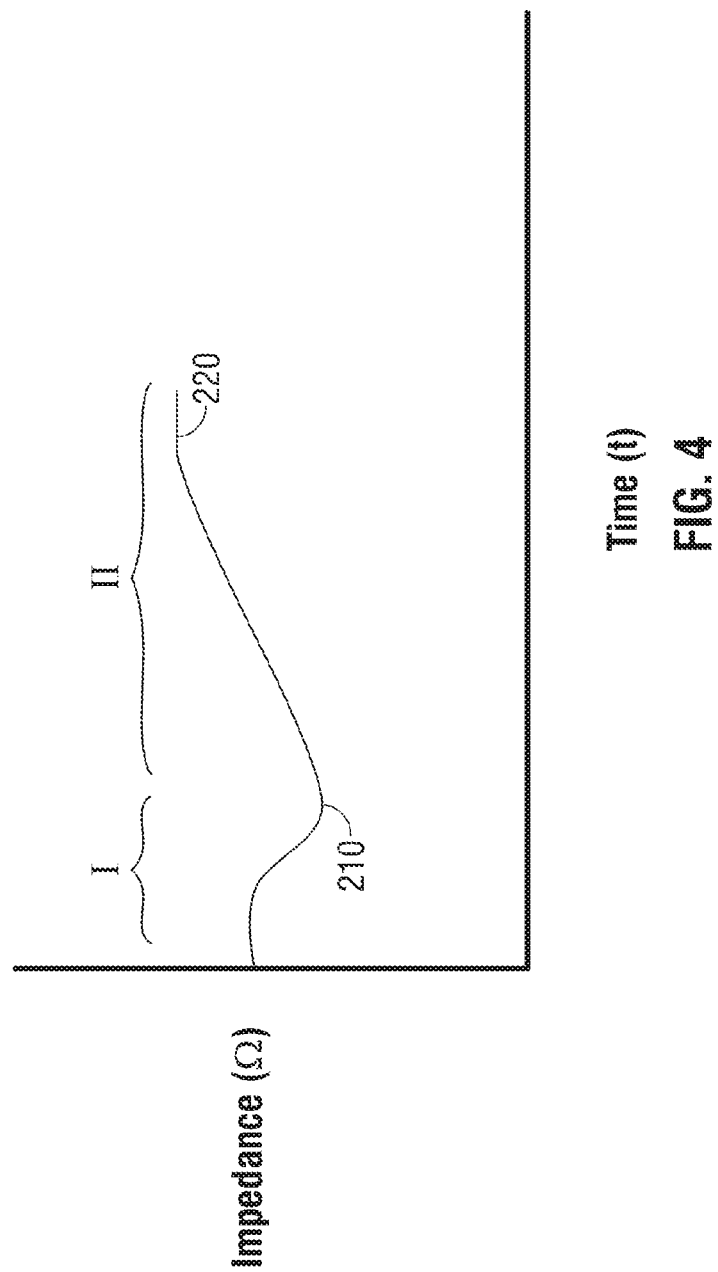
FIG. 4 shows a graph illustrating the changes occurring in tissue impedance over time during an electrosurgical procedure utilizing the method shown in FIG. 3.

Referring specifically now to FIG. 3, a method of performing a tissue sealing procedure is described. In step 100, the user selects/adjusts algorithm parameters (e.g., shutoff impedance, current ramp, impedance ramp, etc.) in accordance with a desired tissue seal result. In response thereto, the microprocessor 25 loads the appropriate algorithm parameters into the configuration file and the generator 20 may generate a display, signal, and/or indication depicting the anticipated burst pressure and seal time that will result from the algorithm parameter adjustments selected by the user.

In embodiments, the tissue treatment algorithm simplifies for the user the customization of tissue seal quality. For example, the user may adjust any one or more algorithm parameters or simply select a particular burst pressure or seal time and the algorithm will proportionally adjust appropriate algorithm parameters in response thereto to ensure that the desired burst pressure is achieved for the resulting tissue seal. The selected parameters and/or the proportionally-adjusted parameters are processed by the microprocessor 25 and loaded into the configuration file. By way of example, if the user opts to increase the ending impedance value 220 to increase the resulting burst pressure of the tissue seal, the algorithm processes (e.g., via microprocessor 25) the ending impedance value 220 and calculates any necessary adjustments in other algorithm parameters (e.g., current ramp, dZ/dt, seal time, etc.) to ensure that the desired burst pressure is achieved as efficiently as possible given the selected parameters. Once calculated, the relevant algorithm parameters may be provided by the display screen of the generator 20. In this manner, the user may choose to readjust certain algorithm parameters based on the information provided via the display screen (e.g., seal time) to either increase seal quality, resulting in an increase in seal time, or decrease seal time, resulting in a decrease in seal quality. In another example, the user may opt to select a desired burst pressure. In this scenario, the algorithm automatically adjusts the appropriate parameters proportionally to achieve the desired burst pressure as efficiently as possible. In this manner, tailoring the seal quality is simplified in that the user is not required to adjust specific algorithm parameters relative to each other to achieve a desired result.

In step 110, the instrument 10 engages the tissue and the generator 20 is activated (e.g., by pressing of a foot pedal or handswitch). In step 120, the tissue treatment algorithm is initialized and the configuration file is processed by microprocessor 25.

In step 130, the generator 20 supplies electrosurgical energy to the tissue through the instrument 2 or the forceps 10. During application of energy to the tissue, impedance is continually monitored by the sensor circuitry 22. In particular, voltage and current signals are monitored and corresponding impedance values are calculated at the sensor circuitry 22 and/or at the microprocessor 25. Power and other energy properties may also be calculated based on collected voltage and current signals. The microprocessor 25 stores the collected voltage, current, and impedance within the memory 26.

In step 140, an offset impedance value is obtained. The offset impedance value is used to calculate a threshold impedance value that denotes completion of treatment. The threshold impedance is the sum of the ending impedance value 220 and the offset impedance value. The offset impedance value may be obtained in multiple ways depending on the electrosurgical procedure being performed. For example, the offset impedance may be tissue impedance measured at the time of maximum current being passed through tissue that is required to facilitate a desired tissue effect. Using the threshold impedance value referenced and partially defined by the offset impedance value, rather than simply an absolute value (e.g., the ending impedance value), accounts for different tissue types and varying surgical devices.

Minimum measured impedance, e.g., the minimum impedance value 210, may also be used as the offset impedance value. This is particularly useful when tissue reacts normally in a desiccation process. As shown in FIG. 4, impedance drops from an initial value until the minimum impedance value 210 is reached. After a given time interval, the impedance rises again at the onset of desiccation as tissue reacts. The amount of time required for the reaction to take place and/or the minimum impedance value 210 can help define various treatment parameters by identifying type of tissue, jaw fill or a particular device being used since the minimum impedance value 210 is aligned with the beginning stage of desiccation. Consequently, the offset impedance value can be captured at the point in time when the impedance slope becomes positive, e.g., when the change of impedance over time (dZ/dt) is greater than zero or dZ/dt is approximately zero. Further, the offset impedance value may be calculated from a variety of different methods and utilizing a variety of different parameters such as, for example, the starting tissue impedance, the impedance at minimum voltage, the impedance at either a positive or negative slope change of impedance, and/or a constant value specified within the programming or as specified by the user and loaded in the configuration file. The starting impedance may be captured at the outset of the application of the electrosurgical procedure via an interrogatory pulse.

In step 150, the timing of the reaction period is commenced to ensure that the reaction period does not exceed the reaction timer. Energy application continues until the threshold impedance value is reached before the expiration of the reaction timer. As discussed above, energy application varies for different types of tissues and procedures, therefore it is desirable that the reaction timer, similar to the threshold impedance, is also tailored to suit particular operational requirements. For this purpose, a time offset period is utilized. In particular, the time offset period is added to the reaction timer to extend the duration of energy application. Multiple time offset period values may be hard-coded (e.g., in a look-up table) so that during the procedure an appropriate value is loaded. The user may also select a desired time offset period.

In step 160, the algorithm calculates the target impedance trajectory based on variety of values such as, for example, initial measured impedance, desired rate of change of impedance (dZ/dt), and the like. In particular, the algorithm calculates a target impedance value at each time-step, based on the predefined desired rate of change of impedance over time (dZ/dt). The desired rate of change of impedance may be stored as a variable (e.g., selected by the user) and be loaded during step 100 or may be selected manually or automatically based on tissue type determined by the selected instrument.

The target impedance takes the form of a target trajectory starting from a predetermined point (e.g., initial impedance value and time value corresponding to a point when tissue reaction is considered real and stable). The target trajectory may have a positive or a negative slope and may be linear, non-linear, or quasi-linear depending on the electrosurgical procedure being performed.

In step 170, the algorithm matches measured impedance to the target impedance trajectory. The algorithm adjusts the tissue impedance to match the target impedance. While the algorithm continues to direct the RF energy to drive the tissue impedance to match the specified trajectory, the algorithm monitors the tissue impedance to make the appropriate adjustments and/or corrections.

In step 180, the algorithm determines whether tissue treatment is complete such that output of generator 20 should be terminated. This is determined by monitoring the actual measured impedance to determine if the actual measured impedance is at or above the predetermined threshold impedance. In step 190, the system monitors whether the amount of time to reach the threshold impedance exceeds the reaction timer plus the time offset period. If the impedance is at or above the threshold impedance and/or the sum of the reaction timer and the time offset period has expired then the algorithm is programmed to signal completion of treatment and the generator 20 is shut off or is returned to an initial state. The tissue treatment algorithm may also determine if the measured impedance is greater than threshold impedance for a predetermined period of time. This determination minimizes the likelihood of terminating electrosurgical energy early when the tissue is not properly or completely sealed.

Other tissue and/or energy properties may also be employed for determining termination of treatment, such as for example tissue temperature, voltage, power and current. In particular, the algorithm analyzes tissue properties and then acquires corresponding impedance values and offset times at the specified points in the tissue response or trajectory and these values or times can be stored and/or used as absolute or reference shut-off impedances and/or times in the manner discussed above.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of performing an electrosurgical procedure, comprising the steps of:
   selecting a preset burst pressure parameter using at least one user input control, the preset burst pressure parameter being a pressure at which tissue will burst at a resulting tissue seal;
   adjusting at least one other parameter of a tissue treatment algorithm configured to control supply of energy to tissue to achieve a burst pressure of the resulting tissue seal equal to the selected preset burst pressure parameter;

supplying energy from an energy source to an electrosurgical instrument for application to tissue;

generating a target impedance trajectory based on measured impedance and the at least one other parameter of the tissue treatment algorithm;

adjusting the supply of energy from the energy source to tissue to match tissue impedance to a target impedance value; and adjusting the target impedance value to vary the burst pressure of the resulting tissue seal.

2. The method according to claim 1, further comprising the step of decreasing the at least one other parameter of the tissue treatment algorithm to increase the burst pressure of the resulting tissue seal.

3. The method according to claim 1, further comprising the step of increasing the at least one other parameter of the tissue treatment algorithm to increase the burst pressure of the resulting tissue seal.

4. The method according to claim 1, further comprising the step of increasing a seal time to increase the burst pressure of the resulting tissue seal.

5. The method according to claim 1, further comprising the step of adjusting a predetermined rate of change of impedance to vary the burst pressure of the resulting tissue seal.

6. The method according to claim 1, further including processing a configuration file including the at least one other parameter of the tissue treatment algorithm.

7. The method according to claim 6, further including updating the configuration file to include the preset burst pressure parameter prior to the supply of energy to the tissue.

8. The method according to claim 1, wherein adjusting the at least one other parameter of the tissue treatment algorithm includes decreasing a current ramp rate to cause at least one of an increase in a seal time and an increase in the burst pressure of the resulting tissue seal.

9. The method according to claim 1, wherein adjusting the at least one other parameter of the tissue treatment algorithm includes decreasing an impedance ramp rate to cause at least one of an increase in seal time and an increase in the burst pressure of the resulting tissue seal.

10. The method according to claim 1, further including generating a threshold impedance value as a function of an offset impedance value and an ending impedance value.

11. The method according to claim 1, further including comparing tissue impedance to a threshold impedance value and adjusting the supply of energy to tissue when the tissue impedance is equal to or greater than the threshold impedance value.

12. The method according to claim 1, further including selecting the at least one other parameter of the tissue treatment algorithm from the group consisting of a current ramp rate, a tissue impedance ramp rate, and an ending impedance value.

13. A method of performing an electrosurgical procedure, comprising the steps of:

selecting a preset burst pressure parameter using at least one user input control, the preset burst pressure parameter being a pressure at which tissue will burst at a resulting tissue seal;

adjusting at least one other parameter of a tissue treatment algorithm configured to control supply of energy to tissue to achieve a burst pressure of the resulting tissue seal equal to the selected preset burst pressure parameter;

supplying energy from an energy source to an electrosurgical instrument for application to tissue;

generating a target impedance trajectory based on measured impedance and a predetermined rate of change of impedance; and adjusting the supply of energy from the energy source to tissue to match tissue impedance to a target impedance value.

14. The method according to claim 13, further comprising the step of adjusting the predetermined rate of change of impedance to adjust the burst pressure of the resulting tissue seal.

15. The method according to claim 13, further comprising the step of automatically adjusting the at least one other parameter of the tissue treatment algorithm relative to at least one further parameter of the tissue treatment algorithm to achieve a bust pressure of the resulting tissue seal equal to the selected preset burst pressure parameter.

* * * * *